(12) United States Patent
Tamura et al.

(10) Patent No.: US 7,575,884 B2
(45) Date of Patent: *Aug. 18, 2009

(54) TEST PIECE FOR MEASURING HIGH-DENSITY LIPOPROTEIN (HDL) CHOLESTEROL

(75) Inventors: Hiroshi Tamura, Kyoto (JP); Susumu Nishino, Kyoto (JP); Takehiro Yamaguchi, Kyoto (JP); Koichi Hino, Tokyo (JP)

(73) Assignees: ARKRAY, Inc., Kyoto (JP); Daiichi Pure Chemicals Co., Ltd., Tokyo (JP)

( * ) Notice: Subject to any disclaimer, the term of this patent is extended or adjusted under 35 U.S.C. 154(b) by 317 days.

This patent is subject to a terminal disclaimer.

(21) Appl. No.: 11/184,117

(22) Filed: Jul. 19, 2005

(65) Prior Publication Data

US 2005/0250165 A1    Nov. 10, 2005

Related U.S. Application Data

(62) Division of application No. 10/415,726, filed on May 1, 2003, now Pat. No. 6,939,682.

(51) Int. Cl.
*C12Q 1/60* (2006.01)
*C12Q 1/44* (2006.01)
*C12Q 1/32* (2006.01)
*C12Q 1/28* (2006.01)
*C12N 11/00* (2006.01)

(52) U.S. Cl. .............................. 435/11; 435/19; 435/26; 435/28; 435/174

(58) Field of Classification Search ....................... None
See application file for complete search history.

(56) References Cited

U.S. PATENT DOCUMENTS

| | | | |
|---|---|---|---|
| 5,426,030 A | 6/1995 | Rittersdorf et al. | |
| 5,580,743 A | 12/1996 | Rittersdorf et al. | |
| 5,589,347 A | 12/1996 | Arai et al. | |
| 5,691,159 A | 11/1997 | Miyauchi et al. | |
| 5,736,406 A | 4/1998 | Miyauchi et al. | |
| 5,773,304 A | 6/1998 | Hino et al. | |
| 6,794,157 B1 | 9/2004 | Sugiuchi | |
| 6,939,682 B2 * | 9/2005 | Tamura et al. | 435/11 |

FOREIGN PATENT DOCUMENTS

| | | |
|---|---|---|
| EP | 0 272 578 | 6/1988 |
| EP | 0 913 484 | 5/1999 |
| EP | 1 046 716 | 10/2000 |
| EP | 1 197 564 | 4/2002 |
| GB | 1 502 152 | 2/1978 |
| JP | 63-158000 | 6/1988 |
| JP | 2-210265 | 8/1990 |
| JP | 3-99268 | 4/1991 |
| JP | 5-80056 | 3/1993 |
| JP | 7-301636 | 11/1995 |
| JP | 8-131197 | 5/1996 |
| JP | 8-201393 | 8/1996 |
| JP | 2600065 | 1/1997 |
| JP | 2799835 | 7/1998 |
| JP | 11-56395 | 3/1999 |
| JP | 2000-325097 | 11/2000 |

* cited by examiner

*Primary Examiner*—David M Naff
(74) *Attorney, Agent, or Firm*—Hamre, Schumann, Mueller & Larson, P.C.

(57) ABSTRACT

The present invention relates to a test piece having a simple structure, by which HDL cholesterol can be measured easily using a small amount of specimen. A reagent layer (2) is formed on a support (1), and an enzyme reagent for measuring cholesterol, a first surfactant that makes a solubility of a high-density lipoprotein (HDL) higher than that of a lipoprotein other than the HDL, and a second surfactant that inhibits the lipoprotein other than the HDL from dissolving are contained in the reagent layer (2).

35 Claims, 4 Drawing Sheets

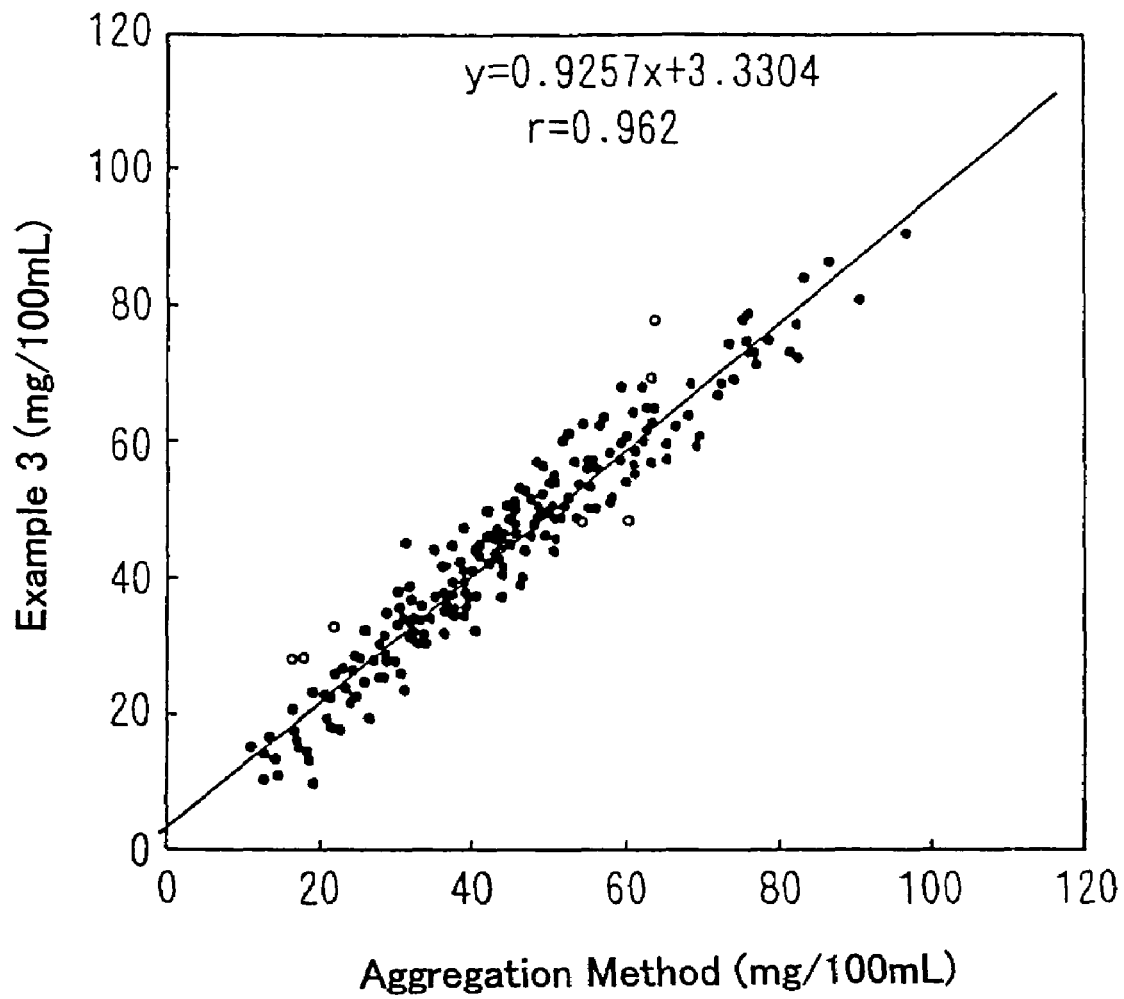
F I G. 3

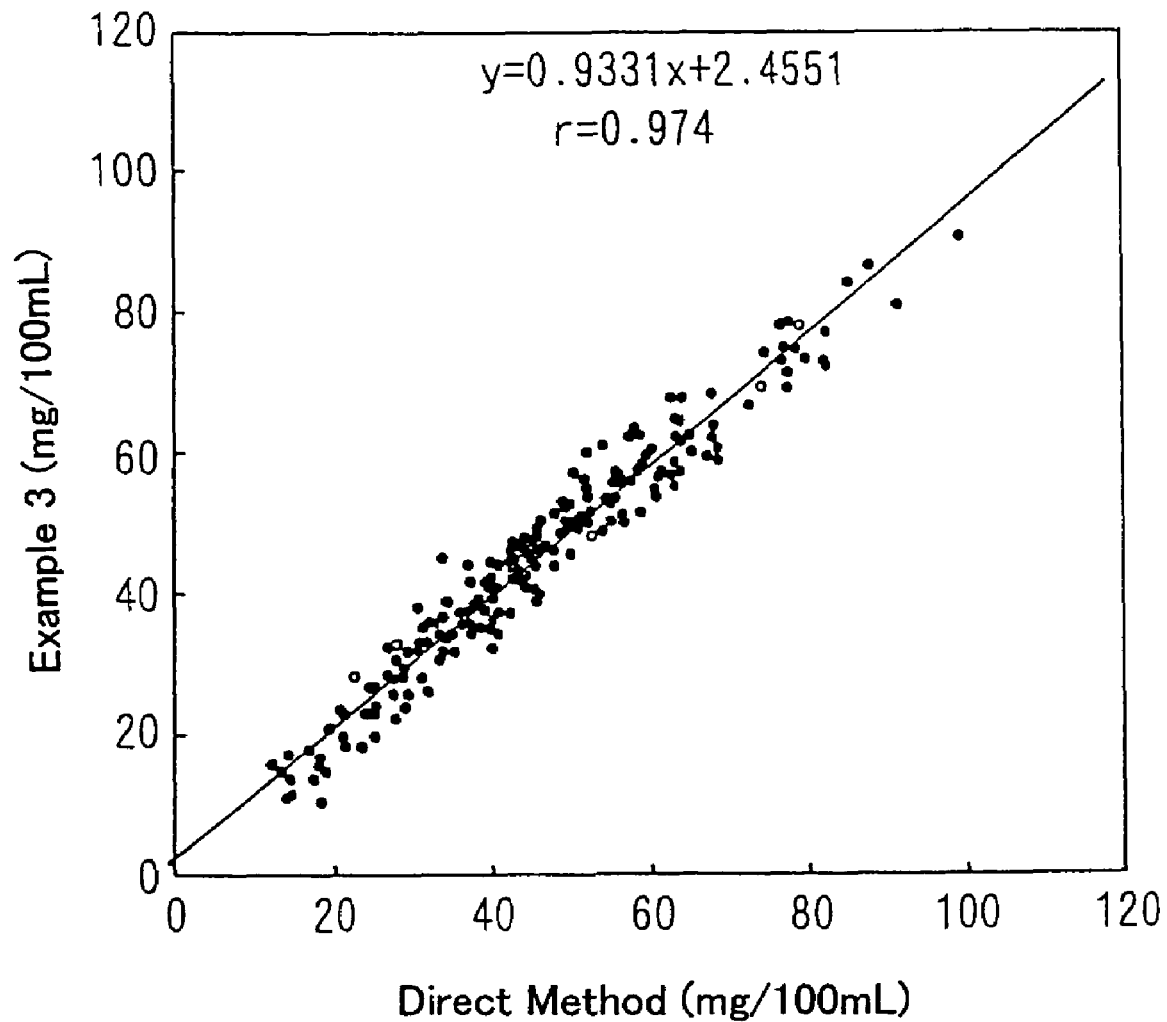
F I G. 4

TEST PIECE FOR MEASURING
HIGH-DENSITY LIPOPROTEIN (HDL)
CHOLESTEROL

This application is a division of application Ser. No. 10/415,726, filed 1 May 2003, now U.S. Pat. No. 6,939,682, entitled TEST PIECE FOR MEASURING HIGH-DENSITY LIPOPROTEIN (HDL) CHOLESTEROL.

TECHNICAL FIELD

The present invention relates to a test piece for measuring high-density lipoprotein (HDL) cholesterol.

BACKGROUND ART

HDL cholesterol is one of the important items to be measured in medical examinations, various tests for clinical medicine, and the like, from the epidemiological viewpoint that the HDL cholesterol is correlated inversely with the frequency of the occurrence of coronary diseases. On the other hand, in clinical tests and the like, test pieces produced by impregnating filter paper or the like with a reagent and then drying it have been used widely because it is necessary to treat a large number of specimens.

One example of a method for measuring HDL cholesterol is separating HDL and other lipoproteins (such as LDL and VLDL) by ultracentrifugation, and then measuring only HDL cholesterol using an enzyme. Another example of the method is separating HDL and other lipoproteins by electrophoresis and staining the lipid to measure the intensity of the color developed. Although they are general methods for measuring HDL cholesterol, they are not practiced in the clinical tests or the like because they require a complicated operation, which makes it difficult to treat a large number of specimens. On this account, a variety of methods for measuring HDL cholesterol that enable the treatment of a large number of specimens have been proposed and are practiced actually in some clinical tests and the like. Examples of such methods will be described in the following.

For example, there have been proposed chemically modifying cholesterol esterase and cholesterol oxidase and specifically reacting the cholesterol in HDL in the presence of an inclusion compound such as cyclodextrin (JP 7(1995)-301636 A); adding an aggregating agent to a specimen to aggregate and settle lipoproteins other than HDL and then measuring HDL cholesterol present in the supernatant (for example, JP 8(1996)-131197 A, Japanese Patent No. 2600065, JP 8(1996)-201393 A, and Japanese Patent No. 2799835); and using a surfactant to generate a time period in which an enzyme reacts with HDL cholesterol specifically and measuring the HDL cholesterol in this time period (JP 11(1999)-56395 A). However, these methods are measurement methods applicable to a liquid system and cannot be applied directly to a test piece, which is a measurement method employing a dry system.

Examples of a method for measuring HDL cholesterol using a test piece include a method utilizing the above-described aggregation reaction (JP 2(1990)-210265 A, JP 3(1991)-99268 A, etc.). However, this method has a drawback in that it requires a filter separation mechanism or the like so that the structure of the test piece becomes complicated and a large amount of specimen is required.

DISCLOSURE OF INVENTION

The present invention has been made in view of the above-described circumstances. It is an object of the present invention to provide a test piece having a simple structure, by which HDL cholesterol can be measured easily using a small amount of specimen.

In order to achieve the above-described object, a test piece for measuring HDL cholesterol according to the present invention includes: an enzyme reagent for measuring cholesterol; a first surfactant that makes a solubility of HDL higher than that of a lipoprotein other than the HDL; and a second surfactant that inhibits the lipoprotein other than the HDL from dissolving.

As described above, by letting the two types of surfactants be contained in the test piece of the present invention, the enzyme reagent for measuring cholesterol can measure the HDL cholesterol specifically and easily. Further, this test piece does not utilize any special reaction such as an aggregation reaction and thus does not require any special structure. Therefore, the test piece of the present invention can have a simple structure and requires only a small amount of specimen.

The test piece according to the present invention may have a structure in which a reagent layer is formed on a support, and the enzyme reagent, the first surfactant, and the second surfactant are contained in the reagent layer. In this case, the reagent layer may include a sample supply layer and a detecting layer. The first surfactant and the second surfactant may be contained in the sample supply layer and the enzyme reagent may be contained in the detecting layer. Further, it is preferable that, inside the sample supply layer, the second surfactant is contained in an upper portion (an upper layer) and the first surfactant is contained in a lower portion (a lower layer). Furthermore, it is also preferable that the first surfactant, the second surfactant, and a part of the enzyme reagent are contained in the sample supply layer, and the rest of the enzyme reagent is contained in the detecting layer.

As the first reagent, polyoxyethylene alkylene phenyl ether and polyoxyethylene alkylene tribenzyl phenyl ether are preferable, which may be used alone or in combination. Of these two surfactants, polyoxyethylene alkylene tribenzyl phenyl ether is more preferable.

As the second reagent, polyoxyethylene alkylether, polyoxyethylene alkyl phenyl ether, a polyoxyethylene-polyoxypropylene condensation product, polyoxyethylene alkylether sulfate, and alkyl benzenesulphonate are preferable, which may be used alone or in a combination of two or more types. Among these, the polyoxyethylene-polyoxypropylene condensation product is the most preferable.

As the enzyme reagent, a combination of cholesterol esterase and cholesterol oxidase and a combination of cholesterol esterase and cholesterol dehydrogenase are preferable. Of these two combinations, the former is more preferable. After the sample is added and mixed with the reagents, the proportion of the cholesterol esterase is, for example, in the range from 5 to 1000 U/mL, preferably from 10 to 100 U/mL, and more preferably from 30 to 70 U/mL. The proportion of the cholesterol oxidase in all the components during the enzyme reaction is, for example, in the range from 5 to 1000 U/mL, preferably from 10 to 100 U/mL, and more preferably from 20 to 50 U/mL. The proportion of the cholesterol dehydrogenase in all the components during the enzyme reaction is, for example, in the range from 5 to 1000 U/mL, preferably from 10 to 100 U/mL, and more preferably from 30 to 70 U/mL. As the enzymes, commercially available enzymes can be used. However, considering the principles of reaction in the present invention, it is preferable to use pure products in which a contaminant that interferes with the reaction steps (e.g., a substance that might degrade the characteristics of the first surfactant or the second surfactant) is not present, e.g., gene recombination products and the like. In the present invention, the proportion in all the components during the enzyme reaction refers to the proportion in all the components after the specimen (sample) has been added, and all the components refers to the components present during the enzyme reaction altogether, such as the sample, the enzyme reagent, the first surfactant, and the second surfactant. Generally, the amount of one specimen can be predicted or determined from the type thereof.

The proportion of the first surfactant in all the components during the enzyme reaction preferably is in the range from 1 to 10 wt %, more preferably from 3 to 7 wt %. On the other hand, the proportion of the second surfactant in all the components during the enzyme reaction preferably is in a range from 1 to 20 wt %, more preferably from 7 to 13 wt %. It is to be noted here that the proportion of these surfactants is considerably higher than that in the case where a liquid system is employed. The weight ratio (A/B) of the first surfactant (A) to the second surfactant (B) preferably is in the range from 1/10 to 1/1, more preferably from 1/3 to 2/3. Further, it is preferable that the reaction pH at the test piece according to the present invention is adjusted to be in the range from 6 to 9. The pH in the range from 7 to 8 is more preferable, and the optimal pH is 7.7.

A specimen to be measured with the test piece according to the present invention in not specifically limited, and may be any specimens (especially biological liquids) that may contain HDL cholesterol, such as whole blood, plasma, and serum, for example.

BRIEF DESCRIPTION OF DRAWINGS

FIG. 3 is a graph showing a correlation between the measured value of HDL cholesterol obtained by a test piece according to still another example of the present invention and the measured value of the same obtained by the aggregation method.

FIG. 4 is a graph showing a correlation between the measured value of HDL cholesterol obtained by a test piece according to still another example of the present invention and the measured value of the same obtained by the direct method.

BEST MODE FOR CARRYING OUT THE INVENTION

Figure 1:
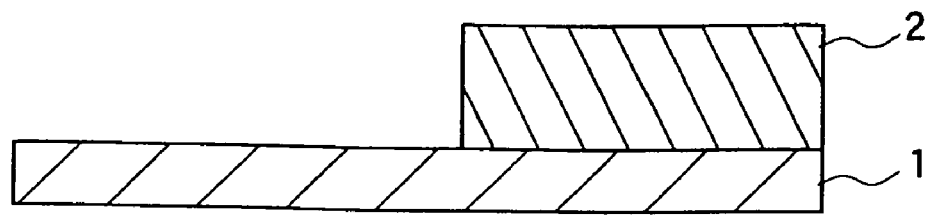
FIG. 1(A) is a cross-sectional view showing a structure of a test piece according to one example of the present invention.
FIG. 1(B) is a cross-sectional view showing a structure of a test piece according to another example of the present invention.
FIG. 1(C) is a cross-sectional view showing a structure of a test piece according to still another example of the present invention.
Figure 1:
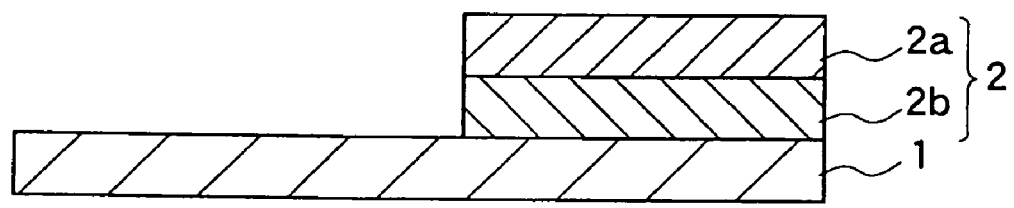
Figure 1:
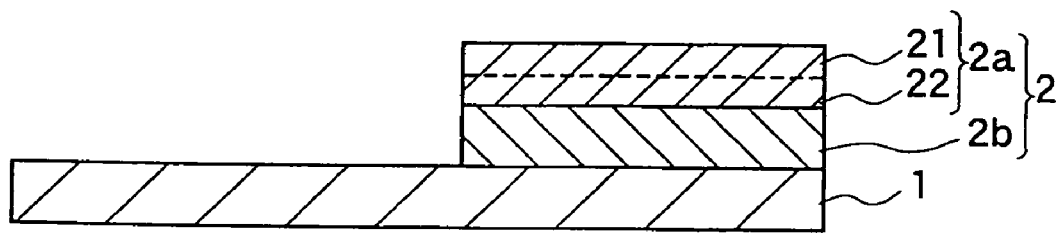

Hereinafter, a test piece of the present invention will be described by way of examples.

First, as an enzyme reagent for measuring cholesterol to be used in the present invention, the above-described two combinations can be used, for example, and the combination of cholesterol esterase and cholesterol oxidase preferably is used. HDL cholesterol in vivo generally is divided into two types depending on its state, i.e., a free state and the state where it is bound to a fatty acid by an ester linkage. Thus, the HDL cholesterol in the latter state is degraded hydrolytically with the cholesterol esterase to generate cholesterol and the fatty acid. Thereafter, the cholesterol thus generated is treated with the cholesterol oxidase to generate cholestenone and hydrogen peroxide. Then, by measuring the hydrogen peroxide, the amount of the HDL cholesterol can be obtained. The measurement of the hydrogen peroxide can be carried out by an electrochemical measuring method or a chemical measuring method. However, a chemical measuring method using a peroxidase (POD) and a substrate that develops color by oxidation (hereinafter, referred to as "oxidation color-developing substrate") preferably is used. In this case, the degree of color development of the oxidation color-developing substrate can be measured optically. Thus, in this case, the enzyme reagent includes the POD and the oxidation color-developing substrate. The proportion of the POD in all the components during the enzyme reaction is in the range from 50 to 5000 U/mL, preferably from 100 to 1500 U/mL, and more preferably from 700 to 800 U/mL, for example. The proportion of the oxidation color-developing substrate in all the components during the enzyme reaction may be determined as appropriate, depending on the types thereof or the like. However, for example, the proportion is in the range from 10 to 1000 mmol/L, preferably from 20 to 200 mmol/L, and more preferably from 30 to 70 mmol/L.

Examples of the oxidation color-developing substrate include: ALPS [N-Ethyl-N-(3-sulfopropyl) aniline sodium salt]; DAOS [N-Ethyl-N-(2-hydroxy-3-sulfopropyl)-3,5-dimethoxyaniline sodium salt]; MAOS [N-Ethyl-N-(2-hydroxy-3-sulfopropyl)-3,5-dimethylaniline sodium salt monohydrate]; TOOS [N-Ethyl-N-(2-hydroxy-3-sulfopropyl)-3-methylaniline, sodium salt dihydrate]; and phenols. Among these, the substrate that develops color measurable at a wavelength used by a measuring apparatus can be selected as appropriate.

The first surfactant is not specifically limited, as long as it can make the solubility of HDL higher than that of other lipoproteins (such as LDL and VLDL). The first surfactant has a function of solubilizing cholesterol or cholesterol esters contained in the HDL, which brings about the effect that the reaction between the cholesterol or esters thereof and the enzyme reagent is accelerated. As the first surfactant, commercially available products may be used. An example of a commercially available polyoxyethylene alkylene phenyl ether is a product named "EMULGEN A-66" (Kao Corporation), and an example of a commercially available polyoxyethylene alkylene tribenzyl phenyl ether is a product named "EMULGEN B-66" (Kao Corporation).

The second surfactant is not specifically limited, as long as it can inhibit the lipoproteins other than the HDL (such as LDL and VLDL) from dissolving. By inhibiting the dissolution of the lipoproteins other than the HDL by the second surfactant, the reaction between cholesterol or esters thereof contained in the lipoproteins other than the HDL and the enzyme reagent is inhibited. As the second surfactant, the above-described surfactants preferably are used. For example, polyoxyethylene cetyl ether (e.g., a product named "EMULGEN 220" available from Kao Corporation) preferably is used as polyoxyethylene alkylether; polyoxyethylene nonyl phenyl ether (e.g., a product named "EMULGEN 913" available from Kao Corporation) preferably is used as polyoxyethylene alkyl phenyl ether; a product named "Pluronic F-88" available from Asahi Denka Co., Ltd. preferably is used as a polyoxyethylene-polyoxypropylene condensation product; sodium polyoxyethylene lauryl ether sulfate (e.g., a product named "EMAL 20C" available from Kao Corporation) preferably is used as polyoxyethylene alkylether sulfate; and sodium dodecylbenzenesulfonate preferably is used as alkyl benzenesulphonate. They can be used alone or in a combination of two or more types.

By using the first surfactant and the second surfactant in combination as described above, a time period is generated in which the enzyme reagent specifically reacts with HDL cholesterol. By carrying out the measurement in this time period, it becomes possible to measure the HDL cholesterol specifically. This time period is, for example, from 1 minute after the start of the reaction (i.e., after adding the specimen) to 20 minutes after the start of the reaction, preferably from 3 minutes after the start of the reaction to 15 minutes after the start of the reaction, and more preferably from 5 minutes after the start of the reaction to 10 minutes after the start of the reaction. The test piece according to the present invention may include, in addition to the enzyme reagent, the first surfactant, and the second surfactant, other additives such as an antioxidant, an anti-reduction agent, and a reagent for removing an interfering substance, if necessary. Such additives may be contained in the test piece in a proportion causing no damage to the function of the enzyme reagent, the first surfactant, and the second surfactant.

Next, one example of a structure of a test piece according to the present invention is shown in the cross-sectional view of FIG. 1.

In a test piece shown in FIG. 1(A), a reagent layer 2 is formed on a support 1. The above-described enzyme reagent, first surfactant, and second surfactant are contained in this reagent layer 2. The support 1 may be made of a resin such as polyethylene terephthalate (PET), polystyrene, polyester, or cellulose acetate. Among these, PET is preferable. The thickness of the support 1 is not specifically limited, and can be, for example, in the range from 0.1 to 1 mm, preferably from 0.1 to 0.5 mm, and more preferably from 0.2 to 0.3 mm. The reagent layer 2 can be formed, for example, by dissolving the enzyme reagent, the first surfactant, the second surfactant, and a hydrophilic polymer in a solvent, applying the resultant mixture onto the support 1 and then drying it. Examples of the hydrophilic polymer include polyvinylpyrrolidone, hydroxypropylcellulose, methylcellulose, sodium alginate, polyacrylic acid, gelatin, acid-hydrolytically-degraded gelatin, polyacrylamide, and agarose. Examples of the solvent include a phosphate buffer, Good's buffers, and a Tris-HCl buffer. Among these, the Good's buffers are preferable. As the Good's buffers, PIPES, TES, HEPES, DIPSO, TAPSO, and MES are preferable, and TES are more preferable. The pH of the buffer is adjusted preferably to be in the range from 6 to 9, more preferably from 7 to 8, and optimally to be 7.7. The proportion of the hydrophilic polymer is, for example, in the range from 0 to 40 wt %, more preferably from 10 to 30 wt % of the total weight of the solution to be applied onto the support 1, and can be adjusted as appropriate, depending on the type thereof. The reagents such as the enzyme reagent, the first surfactant, and the second surfactant are adjusted before being added to the solvent so that they are contained in the resultant solution in the above-described proportions. Further, the method for applying the solution is not specifically limited, and can be, for example, a method using a brush or the like, spray coating, a method using a roll coater, and dipping. The thickness of the reagent layer 2 is, for example, in the range from 50 to 250 μm, preferably from 80 to 200 μm, and more preferably from 100 to 150 μm. The reagent layer 2 may contain the above-described additives such as an antioxidant, if necessary, in addition to the above-described components. The shape of the test piece is not specifically limited. However, the test piece generally has a plate-like shape or a strip shape. In the case where the test piece has a strip shape, the size of the test piece is, for example, in the range from 50 to 150 mm for total length and in the range from 30 to 15 mm for width, and preferably in the range from 60 to 100 mm for total length and in the range from 5 to 10 mm for width.

The test piece can be used in the following manner, for example. First, a specimen such as blood is dripped on the reagent layer 2. The specimen dripped reacts with the reagents contained in the reagent layer 2, and a time period in which the enzyme reagent specifically reacts with HDL cholesterol is generated by the action of the first surfactant and the second surfactant. Then, after the start of the reaction (i.e., after dripping the specimen), the HDL cholesterol is measured in the above-described time period. When the reagent layer 2 contains POD and the oxidation color-developing substrate, the color development of the substrate is measured with an optical measuring apparatus such as a spectrophotometer or a reflectometer. In the case where the sample is plasma or serum, the color development can be measured in the following manner. When the support 1 is optically transparent, the test piece is irradiated with light from the support 1 side or the reagent layer 2 side and the transmitted light or the reflected light is measured. On the other hand, when the support is not optically transparent, it is preferable that the test piece is irradiated with light from the reagent layer 2 side and a reflectance or the like is measured. Further, in the case where the sample is whole blood as will be described later, the color of red blood cells interferes with the measurement of light. On this account, it is preferable to provide a known blood-cell shielding layer and light-reflecting layer between the detecting layer and the sample supply layer, use an optically transparent support, and carry out the measurement from this support side.

Next, in a test piece shown in FIG. 1(B), a detecting layer 2b is formed on a support 1, and a sample supply layer 2a is formed on the detecting layer 2b. A reagent layer 2 is formed of the detecting layer 2b and the sample supply layer 2a. The first surfactant and the second surfactant are contained in the sample supply layer 2a, and the enzyme reagent is contained in the detecting layer 2b. The reagent layer 2 can be formed in the following manner, for example. First, the detecting layer 2b is formed by applying a solution prepared by dissolving the enzyme reagent and a hydrophilic polymer in a solvent onto the support 1 and drying it. On the other hand, a porous member is impregnated with a solution in which the first surfactant and the second surfactant are dissolved and dried. The porous member serves as the sample supply layer 2a after being laminated on the detecting layer 2b, whereby the reagent layer 2 is formed. In this case, the type and the concentration of the hydrophilic polymer and the solvent are as described above. Further, as described above, the sample supply layer 2a preferably is porous. As the porous member, knit fabric can be used, for example. Examples of the knit fabric include polyethylene knit fabric, polyester knit fabric, polytetrafluoroethylene knit fabric, polysulfone knit fabric, polypropylene knit fabric, polyvinylidene difluoride knit fabric, cellulose mixed ester knit fabric, and glass fiber knit fabric. The thickness of the sample supply layer 2a is, for example, in the range from 50 to 400 μm, preferably from 200 to 300 μm, and more preferably from 220 to 270 μm. The thickness of the detecting layer 2b is, for example, in the range from 5 to 100 μm, preferably from 5 to 50 μm, and more preferably from 5 to 20 μm. This test piece can be used in the same manner as in the above-described example. In this test piece, a specimen contacts with the enzyme reagent after having contacted with the first surfactant and the second surfactant, which allows HDL cholesterol to be measured more specifically. Further, as described above, it is preferable that the sample supply layer contains the above-described two types of the surfactants and a part of the enzyme reagent, and the detecting layer contains the rest of the enzyme reagent. For example, cholesterol esterase, cholesterol oxidase, the first surfactant, and the second surfactant may be contained in the sample supply layer and the rest of the enzyme reagent, such as POD and the oxidation color-developing substrate, may be contained in the detecting layer.

In the test piece of the example shown in FIG. 1(B), the sample supply layer 2a may include an upper layer and a lower layer inside, and the second surfactant may be contained in the upper layer and the first surfactant may be contained in the lower layer. FIG. 1(C) shows a test piece according to this example. In FIG. 1(C), numeral 21 denotes an upper layer of a sample supply layer 2a, and numeral 22 denotes a lower layer of the sample supply layer 2a. Other than these, components in common between FIG. 1(B) and FIG. 1(C) are numbered identically. According to this structure, a specimen first contacts with the second surfactant, then contacts with the first surfactant, and finally contacts with the enzyme reagent. This allows HDL cholesterol to be measured still more specifically. The sample supply layer 2a with this structure can be formed in the following manner, for example. After a detecting layer 2b is formed in the above-described manner, a solution prepared by dissolving the first surfactant and a hydrophilic polymer in a solvent is applied onto the detecting layer 2b and dried, and thereafter, a solution prepared by dissolving the second surfactant and a hydrophilic polymer in a solvent further is applied thereto and dried. In this case, the type and the concentration of the hydrophilic polymer and the solvent are as described above, and the method for applying the solutions is also as described above. The method for forming the test piece shown in FIG. 1(C) is not limited to applying the solutions successively, and may be as follows. First, the lower layer is formed by impregnating a porous member with the first surfactant. Then, the upper layer is formed by applying the second surfactant onto one surface of the porous member. Thereafter, the porous member is laminated on the detecting layer 2b so that the lower layer is in contact with the detecting layer 2b, thereby forming the test piece shown in FIG. 1(C).

Further, if necessary, a test piece according to the present invention further may include a blood-cell separating layer on a reagent layer. As the blood-cell separating layer, a porous member capable of filtering blood cells may be provided, and in some cases, a known reflecting layer may be provided along with the porous member. As the porous member, a known blood-cell separating material such as a glass filter can be used, for example. According to the test piece provided with the blood-cell separating layer as described above, HDL cholesterol in serum or plasma can be measured by supplying whole blood as it is.

EXAMPLES

Hereinafter, examples of the present invention will be described along with comparative examples. In the following description, a "K/S" value refers to a variable obtained by the following equation. The K/S value is used when converting a reflectance (R) into a concentration.

$K/S=(1-R)^2/2R$

R: reflectance

Example 1

A solution for forming a detecting layer, having the following composition, was applied onto a white PET film (125 µm thickness) so as to be 150 µm in thickness and then dried at 40° C. for 10 minutes. Thus, a detecting layer was formed. On the other hand, a polyethylene knit fabric (250 µm thickness) was impregnated with an impregnating solution having the following composition, and then dried at 40° C. for 10 minutes. After that, a coating solution was applied onto one surface of the polyethylene knit fabric and then dried at 40° C. for 10 minutes. Thus, a sample supply layer was formed. Subsequently, distilled water was sprayed over the surface of the detecting layer, and the sample supply layer was laminated on the surface of the detecting layer so that the surface of the sample supply layer opposite to the surface onto which the coating solution had been applied was in contact with the surface of the detecting layer. The thus-obtained laminate was then dried at 40° C. for 10 minutes. Thus, a desired test piece was produced. This test piece had a structure as shown in FIG. 1(C). Further, compositions of the respective solutions shown in the following indicate a final concentration (i.e., the concentration during the enzyme reaction) when 5 µL of a sample was supplied. The reaction pH at this test piece during the enzyme reaction was 7.7.

| (Composition of Impregnating Solution) | |
|---|---|
| TES buffer (Dojindo Laboratories, pH 7.7) | 30 mmol/L |
| cholesterol esterase | 39 U/mL |
| cholesterol oxidase | 23 U/mL |
| polyoxyethylene alkylene tribenzyl phenyl ether (Kao Corporation, product name EMULGEN B66) | 5 wt % |

| (Composition of Coating Solution) | |
|---|---|
| polyoxyethylene-polyoxypropylene condensation product (Asahi Denka Co., Ltd., product name Pluronic F-88) | 10 wt % |

| (Composition of Solution for Forming Detecting Layer) | |
|---|---|
| POD (Toyobo Co., Ltd.) | 693 U/mL |
| 4-aminoantipyrine (Kishida Chemical Co., Ltd.) | 43 mmol/L |
| DAOS (Dojindo Laboratories) | 51 mmol/L |
| TES buffer (Dojindo Laboratories, pH 7.7) | 300 mmol/L |

Comparative Example 1 and Comparative Example 2

A test piece was produced in the same manner as in Example 1 except that neither polyoxyethylene alkylene tribenzyl phenyl ether (the first surfactant) nor the polyoxyethylene-polyoxypropylene condensation product (the second surfactant) was used (Comparative Example 1). Further, a test piece was produced in the same manner as in Example 1 except that only the first surfactant was used (the second surfactant was not used) (Comparative Example 2).

Figure 2:
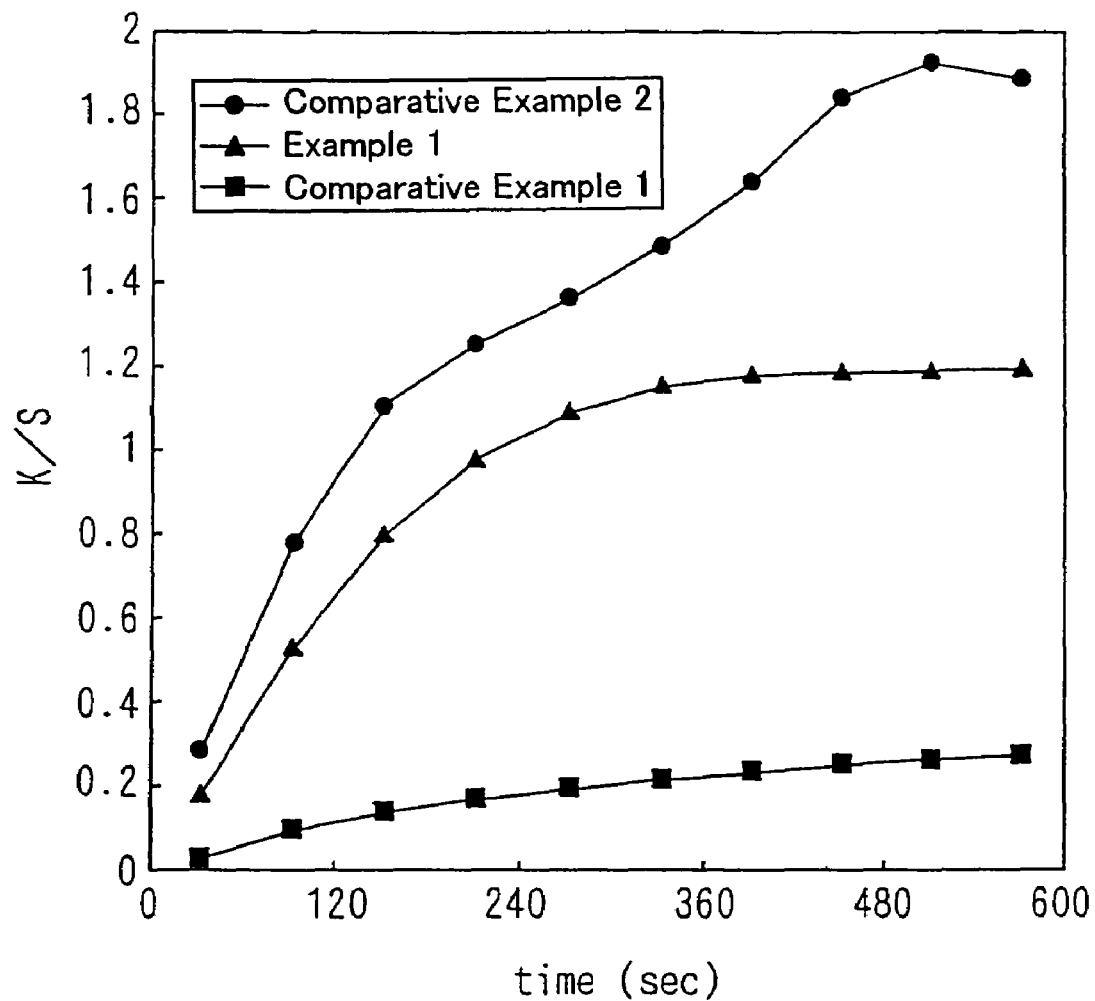
FIG. 2 is a graph showing the change in reflectance overtime in a test piece according to still another example of the present invention.

With regard to the test pieces of Example 1, Comparative Example 1, and Comparative Example 2 produced in the manner described above, a reflectance (time course) was measured with a special-purpose reflectometer (ARKRAY, INC., product name SPOTCHEM) using serum as a sample. The measurement wavelength was 610 nm. The results are shown in the graph of FIG. 2. In this graph, the horizontal axis indicates a measurement time (seconds) and the vertical axis indicates a K/S value described above.

As apparent from the graph of FIG. 2, according to the test piece of Example 1 in which the first surfactant and the second surfactant were used in combination, the reaction terminated in a short time and only the HDL cholesterol could be measured. In contrast, according to the test piece of Comparative Example 1 in which neither of the above-described two surfactants was used, the reaction was weak and the measurement of the HDL cholesterol was substantially impossible. Also, according to the test piece of Comparative Example 2 in which only the first surfactant was used, the HDL cholesterol could not be measured specifically.

Example 2

Three types of test pieces (A, B, C) were produced in the same manner as in Example 1 except that the final concentrations of the first surfactant and the second surfactant were adjusted as shown in Table 1 below. With regard to 60 serum samples with a known HDL cholesterol concentration, a reflectance was measured in the same manner as in Example 1 using these three test pieces. Then, from the reflectance thus measured, the amount of the HDL cholesterol was calculated using the above-described "K/S" value. Then, the correlation between the thus-obtained concentration and the known concentration was examined. The results also are shown in Table 1 below.

TABLE 1

|  | 1st surfactant | 2nd surfactant | correlation coefficient (r) |
|---|---|---|---|
| test piece A | 1 wt % | 1 wt % | 0.87 |
| test piece B | 2 wt % | 2 wt % | 0.94 |
| test piece C | 4 wt % | 4 wt % | 0.97 |

As shown in Table 1, all of these three test pieces A, B, and C exhibited a high correlation coefficient.

Example 3

The same test piece as than of Example 1 was produced. HDL cholesterol in 60 serum samples was measured in the same manner as in Example 2 using this test piece. HDL cholesterol in these samples was measured also by the aggregation method and the direct method as described in the following. Thereafter, the correlations between the measured value obtained by the test piece and that obtained by the aggregation method and between the measured value obtained by the test piece and that obtained by the direct method were examined. The graph of FIG. 3 shows the correlation between the measured value obtained by the test piece and that obtained by the aggregation method. The graph of FIG. 4 shows the correlation between the measured value obtained by the test piece and that obtained by the direct method.

(Aggregation Method)

Using a commercially available kit for measuring HDL cholesterol in serum (Eiken Chemical Co., Ltd., product name HDL-C55), the measurement was carried out in accordance with directions for use thereof. After the reagents and the specimen were mixed with each other, the mixture was centrifuged at 3000 rpm for 10 minutes.

(Direct Method)

Using a commercially available kit for measuring HDL cholesterol in serum (Daiichi Pure Chemical Co., Ltd., product name Cholestest HDL), the measurement was carried out in accordance with directions for use thereof.

As shown in the graph of FIG. 3, there was a strong correlation between the measured value obtained by the test piece and that obtained by the aggregation method. The correlation coefficient was r=0.962. Similarly, as shown in the graph of FIG. 4, there was a strong correlation between the measured value obtained by the test piece and that obtained by the direct method. The correlation coefficient was r=0.974.

INDUSTRIAL APPLICABILITY

As specifically described above, a test piece according to the present invention has a simple structure and can measure HDL cholesterol easily using a small amount of specimen. Therefore, the test piece of the present invention makes it possible to treat a large number of specimens in a short time and thus contributes to improvement in efficiency of clinical tests, in particular.

The invention claimed is:

1. A test piece for measuring high-density lipoprotein (HDL) cholesterol comprising:
    an enzyme reagent for measuring cholesterol;
    a first surfactant that makes a solubility of HDL higher than that of a lipoprotein other than the HDL; and
    a second surfactant that inhibits the lipoprotein other than the HDL from dissolving,
    wherein the enzyme reagent reacts specifically with the HDL cholesterol so as to allow measurement of the HDL cholesterol.

2. The test piece according to claim 1, wherein a weight ratio (A/B) of the first surfactant (A) to the second surfactant (B) is in a range from 1/10 to 2/3, and said test piece is free from an aggregating agent that aggregates lipoproteins other than HDL.

3. The test piece according to claim 2, wherein a reagent layer is formed on a support, and the enzyme reagent, the first surfactant, and the second surfactant are contained in the reagent layer.

4. The test piece according to claim 3, wherein the reagent layer includes a sample supply layer and a detecting layer, the first surfactant and the second surfactant are contained in the sample supply layer, and the enzyme reagent is contained in the detecting layer.

5. The test piece according to claim 4, wherein the second surfactant is contained in an upper portion of the sample supply layer and the first surfactant is contained in a lower portion of the sample supply layer.

6. The test piece according to claim 4, wherein the first surfactant, the second surfactant, and a part of the enzyme reagent are contained in the sample supply layer, and the rest of the enzyme reagent is contained in the detecting layer.

7. The test piece according to claim 2, wherein the first surfactant is at least one surfactant selected from polyoxyethylene alkylene phenyl ether and polyoxyethylene alkylene tribenzyl phenyl ether.

8. The test piece according to claim 2, wherein the second surfactant is at least one surfactant selected from the group consisting of polyoxyethylene alkylether, polyoxyethylene alkyl phenyl ether, a polyoxyethylene-polyoxypropylene condensation product, polyoxyethylene alkylether sulfate, and alkyl benzenesulphonate.

9. The test piece according to claim 2, wherein the enzyme reagent contains cholesterol esterase and cholesterol oxidase.

10. The test piece according to claim 2, wherein the enzyme reagent contains cholesterol esterase and cholesterol dehydrogenase.

11. The test piece according to claim 2, wherein a proportion of the first surfactant in all the components during an enzyme reaction is in a range from 1 to 10 wt %.

12. The test piece according to claim 2, wherein a proportion of the second surfactant in all the components during an enzyme reaction is in a range from 1 to 20 wt %.

13. The test piece according to claim 2, wherein a reaction pH during an enzyme reaction is adjusted to be in a range from 6 to 9.

14. The test piece according to claim 6, wherein the second surfactant is contained in an upper portion of the sample supply layer, the first surfactant and the part of the enzyme reagent are contained in a lower portion of the sample supply layer, and the rest of the enzyme reagent is contained in the detecting layer.

15. The test piece according to claim 6, wherein cholesterol esterase and cholesterol oxidase are contained in the sample supply layer as the part of the enzyme reagent, and a peroxidase and a substrate that develops color by oxidation are contained in the detecting layer as the rest of the enzyme reagent.

16. The test piece according to claim 11, wherein a proportion of the first surfactant in all the components during an enzyme reaction is in a range from 3 to 7 wt %.

17. The test piece according to claim 12, wherein a proportion of the second surfactant in all the components during an enzyme reaction is in a range from 7 to 13 wt %.

18. A method for measuring high-density lipoprotein (HDL) cholesterol in a sample, comprising:
exposing the sample to a test piece comprising an enzyme reagent for measuring cholesterol, a first surfactant that makes a solubility of HDL higher than that of a lipoprotein other than HDL, and a second surfactant that inhibits the lipoprotein other than HDL from dissolving; and
determining an amount of HDL cholesterol in the sample from a reaction of HDL cholesterol with the enzyme reagent,
wherein said test piece is free from an aggregating agent that aggregates lipoproteins other than HDL.

19. The method of claim 18, wherein the test piece comprises an oxidation color-developing substrate and determining the amount of HDL cholesterol comprises measuring color development of the substrate.

20. The method of claim 18, wherein a proportion of the first surfactant in all the components during an enzyme reaction is in a range from 1 to 10 wt %.

21. The method of claim 18, wherein a proportion of the second surfactant in all the components during an enzyme reaction is in a range from 1 to 20 wt %.

22. The method of claim 18, wherein a weight ratio (A/B) of the first surfactant (A) to the second surfactant (B) is in a range from 1/10 to 1/1.

23. The method of claim 18, wherein the test piece comprises a reagent layer formed on a support,
the reagent layer comprises a sample supply layer and a detecting layer,
the first and second surfactants are present in different portions of the sample supply layer, and
at least part of the enzyme reagent is present in the detecting layer.

24. The method of claim 23, wherein the second surfactant is contained in an upper portion of the sample supply layer and the first surfactant is contained in a lower portion of the sample supply layer.

25. The method of claim 23, wherein the first surfactant, the second surfactant, and a part of the enzyme reagent are contained in the sample supply layer, and the rest of the enzyme reagent is contained in the detecting layer.

26. The method of claim 25, wherein the second surfactant is contained in an upper portion of the sample supply layer, the first surfactant and the part of the enzyme reagent are contained in a lower portion of the sample supply layer, and the rest of the enzyme reagent is contained in the detecting layer.

27. The method of claim 25, wherein cholesterol esterase and cholesterol oxidase are contained in the sample supply layer as the part of the enzyme reagent, and a peroxidase and a substrate that develops color by oxidation are contained in the detecting layer as the rest of the enzyme reagent.

28. The method of claim 20, wherein a proportion of the first surfactant in all the components during an enzyme reaction is in a range from 3 to 7 wt %.

29. The method of claim 21, wherein a proportion of the second surfactant in all the components during an enzyme reaction is in a range from 7 to 13 wt %.

30. The method of claim 22, wherein a weight ratio (A/B) of the first surfactant (A) to the second surfactant (B) is in a range from 1/3 to 2/3.

31. The method of claim 18, wherein the first surfactant is at least one surfactant selected from polyoxyethylene alkylene phenyl ether and polyoxyethylene alkylene tribenzyl phenyl ether.

32. The method of claim 18, wherein the second surfactant is at least one surfactant selected from the group consisting of polyoxyethylene alkylether, polyoxyethylene alkyl phenyl ether, a polyoxyethylene-polyoxypropylene condensation product, polyoxyethylene alkylether sulfate, and alkyl benzenesulphonate.

33. The method of claim 18, wherein the enzyme reagent contains cholesterol esterase and cholesterol oxidase.

34. The method of claim 18, wherein the enzyme reagent contains cholesterol esterase and cholesterol dehydrogenase.

35. The method of claim 18, wherein pH is from 6 to 9 during the reaction of HDL cholesterol with the enzyme reagent.

* * * * *